United States Patent [19]

Gluckman et al.

[11] Patent Number: 5,434,134
[45] Date of Patent: Jul. 18, 1995

[54] USE OF HUMAN IGF-1 TO TREAT CARDIAC DISORDERS

[75] Inventors: Peter Gluckman, Auckland, New Zealand; Anna Skottner, Ekerö, Sweden

[73] Assignee: Pharmac IA AB, Sweden

[21] Appl. No.: 84,232

[22] PCT Filed: Jan. 10, 1992

[86] PCT No.: PCT/SE92/00009
§ 371 Date: Oct. 7, 1993
§ 102(e) Date: Oct. 7, 1993

[87] PCT Pub. No.: WO92/11865
PCT Pub. Date: Jul. 23, 1992

[30] Foreign Application Priority Data

Jan. 11, 1991 [SE] Sweden ................. 9100099

[51] Int. Cl.⁶ ............... A61K 38/27; A61K 38/08; A61K 38/00; C07K 14/00
[52] U.S. Cl. ........................ 514/12; 530/399
[58] Field of Search .............. 514/12, 399; 530/399

[56] References Cited

FOREIGN PATENT DOCUMENTS

0176341A1 4/1986 European Pat. Off.
0308386A1 3/1989 European Pat. Off.
0331630A1 9/1989 European Pat. Off.

OTHER PUBLICATIONS

Vasconez et al., Acta Paediatr. Suppl. 399, (37-9) (1944).
Walker et al., NEJM, 324, 1483-1491, (1991).
Fuller, et al., Stimulation of cardiac protein synthesis by Insulin-like growth factors, Biochemical Society Transactions (1991), vol. 19, p. 277S.
Froesch, et al., Actions of Insulin-Like Growth Factors, Ann. Rev. Physiol. (1985), vol. 47, pp. 443-467.
Fuller, et al., Stimulation of protein synthesis, glucose uptake and lactate output by insulin and adenosine deaminase in the rat heart, FEBS 3713, (1986) vol. 201, No. 2, pp. 246-250.
Flaim, et al., Insulin effects on protein synthesis are independent of glucose and energy metabolism, The Am. Psy. Soc., (1983), pp. C133-C143.
Humbel, Insulin-like growth factors I and II, J. Biochem., vol. 190 (1990), pp. 445-462.
Physiological Reviews, The American Physiological Society, vol. 70, No. 3 (1990), pp. 591-614.
Fuller et al., Biochemical Society Transactions, 19, 2777S, 1991.
Balk et al., Life Sciences, 35(4),335-346, 1984.
Fuller, et al., Stimulation of cardia protein synthesis by insulin-like growth factors, Biochem. Soc. Transactions (1991) 19.
Balk, et al., Somatomedins (insulin-like growth factors), but not growth hormone, are mitogenic from chicken heart mesenchymal cells and act synergistically with epidermal growth factor and brain fibroblast growth factor, Life Sciences, vol. 35, pp. 335-346.
Kardami, Stimulation and inhibition of cardiac myocyte proliferation in vitro, Molecular and Cellular Biochemistry 92: 129-135 (1990).
Vetter, et al., Insulin-like growth factors and insulin increase the contractility of neonatal rat cardiocytes in vitro, Basic Research in Cardiology, vol. 83, (1988), pp. 647-654.

Primary Examiner—Howard E. Schain
Assistant Examiner—Phynn Touzeau
Attorney, Agent, or Firm—Pollock, Vande Sande & Priddy

[57] ABSTRACT

Human IGF-I or effective analogues thereof are used for preventing or treating cardiac disorders. Compositions are also provided that comprise human IGF-I or effective analogues thereof together with additional proteins or peptides such as other growth factors, hormones, binding proteins or receptors for enhancing or improving the desired effects of IGF-I or its effective analogues and possibly pharmaceutically acceptable carrier or diluent for the prevention or treatment of cardiac disorders.

13 Claims, 3 Drawing Sheets

USE OF HUMAN IGF-1 TO TREAT CARDIAC DISORDERS

TECHNICAL FIELD

The present invention relates to growth factors, related compounds, and their use in the prevention or treatment of disorders of the heart.

BACKGROUND ART

Insulin-like Growth Factor I (IGF-I) is a peptide present in plasma and other body fluids. It comprises 70 amino acids, including 3 disulphide bonds, and can stimulate growth of a wide range of cell types and it mediates the effects of growth hormone on skeletal growth. Human IGF-I has been purified from plasma and its complete amino acid sequence is established. Sequences with extensive homologies to human IGF-I are present in IGF-I purified from plasma of other species. IGF-I has both systemic and local effects and appears mostly associated with different specific binding proteins, four of which have been sequenced and are termed IGFBP1, IGFBP2, IGFBP3 and IGFBP4. These appear to modulate the biological functions and availability of IGF-I in both positive and negative manners. Analogues with changed affinities for the binding proteins have been produced and changes of biological activities related to sequence variation have been found. IGF-I appears to act mainly by interactions with the IGF-type 1 receptor exposed on the outer surface of plasma membranes in many different cell types. However, binding to IGF type 2- and insulin receptors also seems to be of importance. Because of the scarcity of purified plasma IGF-I there was a great necessity to develop methodology for the commercial scale production of IGF-I. Nowadays, such large scale production can readily be achieved by using recombinant DNA techniques. As a result of studies with preparations of recombinant IGF-I (rIGF-I), it has been demonstrated that rIGF-I promotes skeletal growth and skeletal muscle protein synthesis. Moreover, IGF-I is also effective for the treatment or prevention of catabolic states in patients (Swedish patent application SE 9002731-9) and improves the regeneration of transected periferal nerves (EP 0 308 386). It has previously been demonstrated in vitro that IGF-I also can promote actin synthesis in myocytes in culture (Florini, J. R., Muscle and Nerve 10 (1987)577-598) and contractility of neonatal rat cardiocytes in vitro (Vetter, U et al., Basic Res. Cardiol. 83 (1988)647-654). Prior art has, however, not extended these observations to the whole animal or to therapeutic usefulness.

SUMMARY OF THE INVENTION

In the first aspect of the present invention we have found that a specific biological action of IGF-I or its effective analogues when administered systemically to mammals, including man, is to selectively promote net protein synthesis in heart muscle, i.e. to an extent considerably greater than that seen in other tissues. In a second aspect, systemic administration of IGF-I or an effective analogue has by us been shown to markedly increase the stroke volume of the heart and thereby the cardiac output. Thus, IGF-I or an effective analogue, with or without coadministration of its binding proteins, is according to the present invention a suitable therapy for low cardiac output in man.

The invention discloses a method of preventing or treating cardiac disorders comprising administration of human IGF-I or effective analogues thereof, as well as the use of human IGF-I or effective analogues thereof for the manufacture of a medicament. The use is especially of interest for promotion of cardiac muscle protein synthesis and for treatment of cardiomyopathies, acute heart failure or acute insult including myocarditis or myocardial infarction.

Also disclosed are the uses for: prevention of cardiomyopathies following drug administration, inflammation, infection, sepsis or ischaemia, increasing the rate of recovery from cardiomyopathy, myocarditis, inflammation or myocardial ischaemia and infarction; improvement of cardiac output by increasing stroke volume and for treatment of myocardial infarction. The cardiac output can be reduced as a result of trauma, sepsis, myocardial infarction, surgery, cardiac inflammation or a combination thereof. Preferably human IGF-I is used. The dose given could be 0.01-10, preferably 0.1-1 mg/kg body weight/day. At higher doses, above approximately 2 mg/kg body weight/day hypoglycaemic effects will appear and have to be compensated for (glucose administration).

The administration of human IGF-I or effective analogues thereof can be subcutaneous, intramuscular, intravenous, nasal, oral, dermal or a combination of these administation methods. Preferably the administration route is subcutaneous. The invention also provides a composition comprising human IGF-I, or effective analogues thereof together with additional proteins or peptides such as other growth factors, hormones, binding proteins or receptors for enhancing or improving the desired effect(s) of IGF-I or its effective analogues.

A pharmaceutically acceptable carrier or diluent for the prevention or treatment of cardiac disorders can be added.

The cardiac muscle has several characteristics that are different to what is found in skeletal muscle. The fibers are not syncytial but are made from separate cellular units which are joined together at the ends and they are not cylindrical units, but bifurcate and connect with other fibers to form a network. The nuclei of the cells are also localized deeper than in skeletal muscle cells, and the sarcoplasm contains more mitochondria than in skeletal muscle.

I. Promotion of net protein synthesis in heart muscle

The property of IGF-I or its effective analogues to selectively promote protein synthesis in the heart muscle is useful for prevention or treatment of a variety of primary or secondary cardiac disorders in man, including but not limited to the following:

I:1) To treat cardiomyopathies. These conditions are characterized by insufficient cardiac muscle mass for maintaining sufficient volume output. They may be idiopathic, post-infectious or infiltrative in origin or iatrogenically induced by certain drugs, particularly those used for treatment of leukaemias and other malignancies. The use of IGF-I to selectively increase the net cardiac muscle protein synthesis is claimed in this invention for reduction of morbidity and mortality associated with cardiac myopathy.

I:2) To prevent the onset of cardiomyopathies following the administration of cardiotoxic drugs such as duanorubicin or adriamycin (used in the treatment of malignancy). Cardiac myopathy may be predicted in certain conditions particularly where drugs such as adriamycin or duanorubicin are used. It is claimed that IGF-I through its effects to maintain and promote cardiac muscle net protein synthesis, in these situations will alleviate, or reduce, or prevent development of cardiac myopathy, thus improving the outcome for the patient.

I:3) To improve cardiac muscle retention or restoration following infection, trauma, toxicity, major injury or surgery. Diseases of the heart such as myocarditis may frequently be associated with a rapid and substantial loss of heart muscle mass. Similarly, patients recovering from surgery with septicaemia following acute trauma or other severe illnesses may rapidly lose heart muscle protein causing increased morbidity and mortality. It is claimed that the use of IGF-I in these situations, for promoting cardiac muscle protein net synthesis and preventing cardiac muscle protein loss, will reduce the incidence of morbidity or mortality and shorten the length of hospital stay. Furthermore, promotion of the rate of recovery will indirectly also minimize the incidence of unwanted side effects due to prolonged illness.

I:4.) Promotion of recovery from myocardial infarction. Ischaemia is associated with reduction of cardiac muscle mass in the ischaemic region. Recovery requires scarring, which is the promotion of fibrous tissue deposition, and also functional recovery of the heart muscle bordering on the region of infarction. Inherent in this claim is that IGF-I, which is known to be produced locally in elevated concentrations in various other tissues following trauma or injury, when adminstered systemically promotes cardiac muscle recovery thus hastening functional recovery of the heart and the state of well-being of the patient. As morbidity and mortality following cardiac infarction is associated with a slow rate of recovery, promotion to achieve a more rapid rate of cardiac muscle recovery by the use of IGF-I will reduce morbidity and mortality.

I:5) To improve cardiac muscle function by increasing net protein synthesis and/or the functional capacity of cardiac muscle in conditions of heart muscle damage, including myocarditis (for example secondary to rheumatic fever or a viral infection), following myocardial ischaemia (with or without infarction), or any other cardiac muscle disease.

The properties described above should permit more rapid healing of cardiac muscle following an acute insult such as myocarditis or myocardial infarction.

II Increase of heart stroke volume/Inotropic effect

Situations with insufficient cardiac output may be seen in patients in acute shock, with septicaemia, post-surgery, following infective or toxic illness to the heart such as myocarditis or cardiomyopathy, following ischaemic insult to the heart such as myocardial infarction, etc. In these situations and in any other conditions of insufficient cardiac output it is claimed that IGF-I administration also over longer periods of time is of therapeutic value not only to promote the rate of cardiac muscle recovery but also to maintain cardiac output. Further, because the effect on stroke volume is not paralleled by any pronounced effect on heart rate and because the effect is acute, the use is extended to emergency situations of cardiac failure. Clinical situations include, but are not limited to cardiomyopathy, myocarditis and post myocardial infarction.

More specifically the present invention provides a pharmaceutical composition that includes an effective amount of a peptide or effective analogue of IGF-I and a pharmaceutically-acceptable carrier or diluent. The route of administration may be intravenous, intramuscular, subcutaneous, intranasal, oral or dermal or a combination of these administration methods. The peptide may be present in amounts sufficient to provide a dose rate of approximately 0.01–10, preferably 0.1–1 mg/kg body weight/day.

BEST AND VARIOUS MODES FOR CARRYING OUT INVENTION

Figure 1:
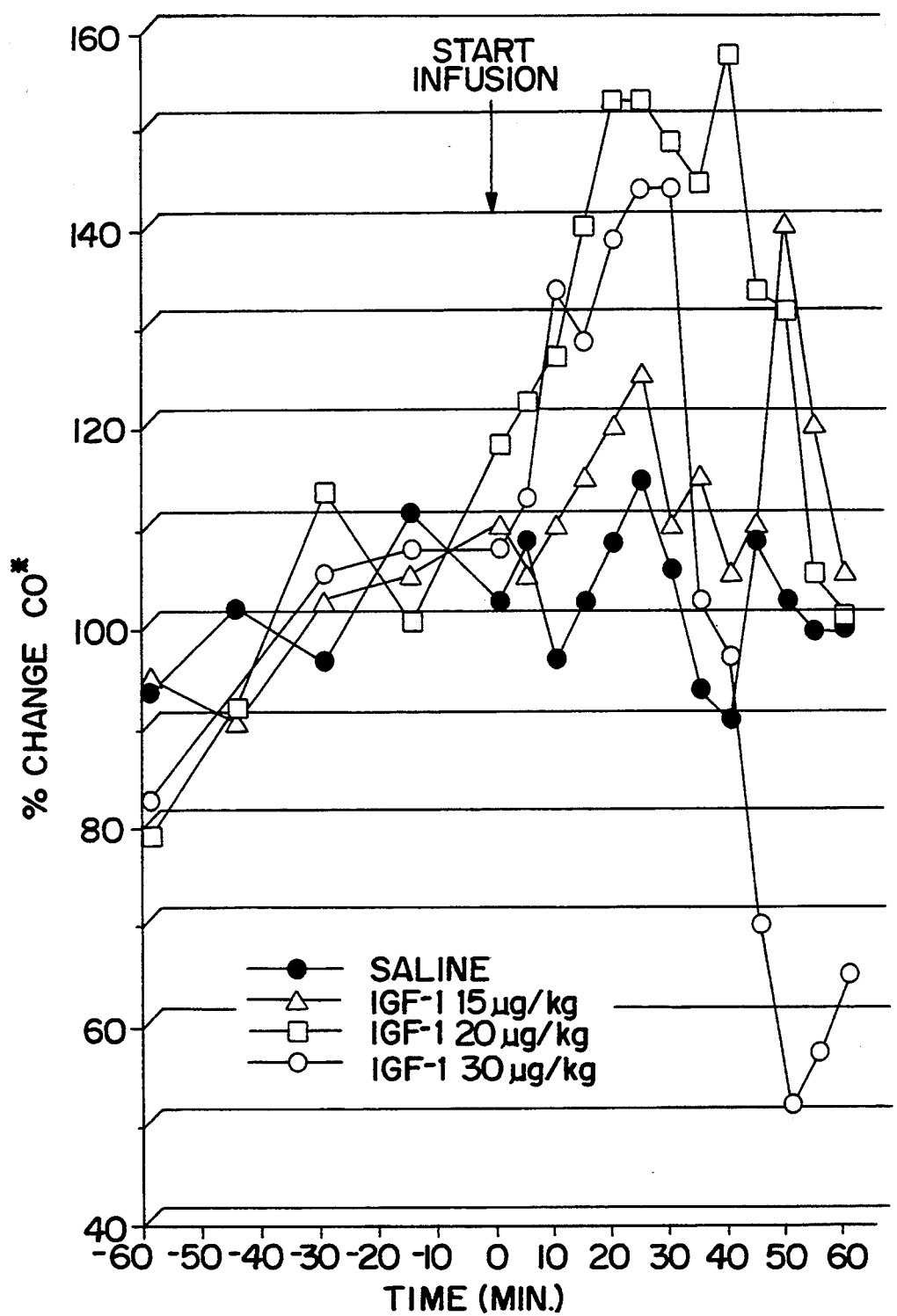
FIG. 1 shows the percentage in cardiac output (CO) following a bolus of rhIGF-I given at time=60 minutes

The preferred form of the invention will now be described with reference to the following non-limiting examples:

I. The effect of IGF-I to promote net protein synthesis in the heart.

EXAMPLES 1

Studies were performed in sheep that had been fasted for 48 hours thus lowering their basal plasma IGF-I levels. They were infused for 5 hours with recombinant human IGF-I at a dose of either 15 or 50 µg/kg/hr.

The lower dose was associated with an approximate doubling of plasma IGF-I concentrations and only a minimal change in binding protein distribution, whereas the higher dose caused a quadrupling of plasma IGF-I levels and some elevation in free (i.e. not bound to binding proteins) plasma IGF-I. Moreover, the lower dose did not affect whole body carbohydrate metabolism whereas the higher dose did so. Controlled studies using an equivalent hypoglycaemic dose of insulin (1 µg/kg/hr) showed no effect on cardiac metabolism demonstrating the IGF-I-specificity of the observed activity.

Cardiac muscle metabolism was determined by incorporation of $^{14}C$-leucine into proteins. Determinations of the incorporation in the diaphragm, skeletal muscles and liver were also performed. IGF-I increased the fractional synthetic rate (FSR) within all tissues examined but the magnitude of induction was considerably greater in cardiac muscle than in any other of the tissues (as shown in Table I). The protein FSR increased from 2.9%/day to 5.6%/day (a 93% increase) in the heart, whereas it in skeletal muscle increased from 0.9%/day to 1.3%/day (a 44% increase).

In the low dose IGF-I group the protein FSR increased by 38% in the heart, whereas no effect was observed in skeletal muscle. Thus, also a low non-hypoglycaemic dose of IGF-I selectively affects cardiac muscle.

These observations provide clear evidence for the unique selectivity for heart muscle of the anabolic effects of systemically administered IGF-I.

TABLE I

Fractional Synthesis Rate (FSR) of Protein (%/day)

| No. | Adductor | Psoas | Diaphragm | Heart | Liver |
|---|---|---|---|---|---|
| | | | Animal Tissue | | |
| | | | Saline: | | |
| 112 | 0.7 | 0.7 | 1.0 | 3.3 | 15.0 |
| 116 | 0.9 | 1.2 | 1.5 | 3.6 | 16.9 |
| 133 | | 1.2 | 1.8 | 3.2 | 7.0 |
| 135 | 0.7 | 0.8 | 1.2 | 1.7 | 7.9 |
| 138 | 0.7 | 0.6 | 0.9 | 2.5 | 8.4 |
| 146 | 0.8 | 0.7 | 1.6 | 3.0 | 11.2 |
| Mean ± SE | 0.8  0.1 | 0.9 ± 0.1 | 1.3 ± 0.1 | 2.9 ± 0.3 | 11.0 ± 1.7 |
| | | | Insulin, 1 μg/kg, h: | | |
| 171 | 0.7 | 1.1 | 1.6 | 5.2 | 19.1 |
| 172 | 0.8 | 0.7 | 1.0 | 2.7 | 10.8 |
| 175 | 0.8 | 1.0 | 1.6 | 4.9 | 15.8 |
| 176 | 0.6 | 0.6 | 1.5 | 3.9 | 11.8 |
| Mean ± SE | 0.7 ± 0.0 | 0.9 ± 0.1 | 1.4 ± 0.1 | 4.2 ± 0.6 | 14.2 ± 2.0 |
| | | | IGF-I, 15 μg/kg, h: | | |
| 158 | 0.8 | 1.0 | 1.5 | 5.1 | 15.4 |
| 159 | 0.7 | 0.8 | 1.3 | 4.0 | 12.8 |
| 160 | 0.7 | 0.7 | 1.1 | 4.2 | 12.3 |
| 161 | 0.6 | 0.5 | 1.0 | 2.8 | 9.6 |
| Mean ± SE | 0.7 ± 0.0 | 0.7 ± 0.1 | 1.3 ± 0.2 | 4.0 ± 0.5 | 12.5 ± 1.2 |
| | | | IGF-I, 50 μg/kg, h: | | |
| 137 | 1.1 | 1.5 | 2.7 | 5.9 | 16.7 |
| 139 | 0.8 | 1.3 | 2.3 | 5.1 | 16.5 |
| 144 | 1.2 | 1.1 | 3.2 | 7.7 | 23.9 |
| 145 | 0.8 | 1.1 | 2.0 | 5.0 | 13.3 |
| 147 | 1.0 | 1.6 | 2.8 | 4.2 | 13.8 |
| 148 | 0.9 | 1.3 | 2.4 | 5.6 | 19.9 |
| Mean ± SE | 1.0 ± 0.1# | 1.3 ± 0.1# | 2.6 ± 0.2• | 5.6 ± 0.5 § | 17.4 ± 1.7# |

\# $p < 0.05$,
§ $< 0.01$,
• $p < 0.005$ compared to normal saline infused controls (Significance levels were not determined on the results from the low dose IGF-I group since it comprised only 4 animals.)

EXAMPLE

Supporting evidence for the physiological significance and potential therapeutic significance of this effect is provided in observations we made in mice selected at 42 days of age for their high or low plasma IGF-I concentrations. After eight generations of selections, two stable lines of mice were achieved; the high level plasma IGF-I mice were longer and heavier than the low level IGF-I mice, irrespective of sex.

An examination of the ratios of organ weights between the two lines of mice shows a disproportionate increase in heart size in the high level IGF-I line mice when compared to the other line of mice. This suggests that chronic exposure to high IGF-I levels is associated with a larger heart due to increase in cardiac muscle mass.

Thus, the example quoted above, showing that acute IGF-I administration can specifically and selectively increase net protein synthesis in heart muscle can be extrapolated to also a chronic situation.

This provides the evidence that therapy with IGF-I, or its analogues, may be used in man to promote cardiac muscle protein synthesis in conditions where this is therapeutically desirable.

II The inotrophic effects of IGF-I

Example 3

Studies were performed in growing lambs with Swan-Ganz catheters passed through the jugular vein through the right side of the heart to the pulmonary artery to measure cardiac output and heart rate. The lambs were studied while conscious and suspended in a sling. Infusions of IGF-I of 50 μg/kg/hr intravenously had no effect on either heart rate or stroke volume. Infusions in excess of 50 μg/kg/hr increased stroke volume during the period of infusion and for approximately 1 hour following the end of the infusion by approximately 75%. Because the stroke volume was increased without any change in heart rate, cardiac output increased analogously.

The increase of stroke volume without changes in heart rate demonstrates that the effect seen relate solely to specific actions of IGF-I rather than indirectly through changes in blood glucose status or in levels of plasma catecholamines. This example provides the basis for the second aspect of the present invention, namely the use of IGF-I in an ailing heart to increase stroke volume without influence on heart rate.

EXAMPLE 4

The studies were performed in cryptorchid ram lambs weighing between 15 and 25 kilograms and 2 to 4 months of age. The animals were fasted for 24 hours prior to study to facilitate a safe general anaesthetic.

General anaesthesia was induced with an intravenous injection of opiate (Saffan). A tracheotomy was established and anaesthesia was maintained with inhaled flourothan (ICI, New Zealand). The effectiveness of anaesthesia was monitored clinically and by sequential measurements of blood pH, $PaCO_2$.

Measurement of Cardiac Output:

By open dissection the right femoral artery and left external jugular vein were cannulated for the measurement of mean arterial pressure and for infusion of fluid respectively. A Swan Ganz catheter was introduced into the pulmonary artery via the right external vein. This was used to measure central venous pressure, core body temperature and to determine cardiac output using the thermodilution technique and a Hewlet Packard Microprocessor. This involved the rapid injection of 5 ml increments of ice cold saline into the pulmonary artery. The animals in each group (three lambs) received the same total volume of saline (60 ml in 1 hour).
Experimental Protocol:

The experimental protocol was of 2 hours duration. Following vascular cannulation and placement of the Swan Ganz catheter a baseline period of 1 hour duration was commenced. Intravenous fluid replacement was commenced to maintain a mean arterial pressure of 90–100 mmHg and a central venous pressure of 10–12 mmHg. During this period cardiac output was determined every 15 minutes. Arterial blood gas values and hemoglobin concentrations were checked and the preparation was abandoned if the hemoglobin concentration was below 80 g/l or the pH below 7.3.

Following the 1 hour baseline period the animal received a bolus of normal saline (n=3), or rhIGF-I at a dose of 15 ug/kg (n=3), 20 ug/kg (n=3) or 30 ug/kg (n=3) and the cardiac output was determined every 5 minutes. No intravenous fluid support other than that required to determine the cardiac output was given during this period.
Analysis of Samples:

The plasma glucose concentration was determined using a Hitachi Autoanalyser (Hitachi, Japan). The plasma concentration of adrenaline and noradrenaline was determined using high performance liquid chromatography. The results are given in Table 2.

TABLE 2

| Time/min) | Plasma glucose, mean ± SE mmol/L | | | |
|---|---|---|---|---|
| | Saline | 15 μg/kg | 20 μg/kg | 30 μg/kg |
| −45 | 3.5 ± 0.2 | 3.7 ± 0.3 | 3.6 ± 0.2 | 3.2 ± 0.1 |
| −30 | 3.5 ± 0.1 | 3.4 ± 0.2 | 3.3 ± 0.2 | 3.3≈0.2 |
| −15 | 3.3 ± 0.3 | 3.5 ± 0.3 | 3.5 ± 0.4 | 3.1 ± 0.3 |
| 0 | 3.5 ± 0.1 | 3.6 ± 0.2 | 3.5 ± 0.2 | 3.2 ± 0.2 |
| 15 | 3.6 ± 0.2 | 3.6 ± 0.2 | 2.6 ± 0.1 | 2.8 ± 0.2 |
| 30 | 3.5 ± 0.1 | 3.8 ± 0.3 | 2.8 ± 0.2 | 2.5 ± 0.3 |
| 45 | 3.4 ± 0.1 | 3.2 ± 0.2 | 3.2 ± 0.3 | 2.9 ± 0.3 |
| 60 | 3.5 ± 0.1 | 3.3 ± 0.3 | 3.2 ± 0.4 | 3.2 ± 0.1 |

The plasma glucose concentration measured following a bolus of saline or IGF-I at a dose of 15 ug/kg was unchanged in comparison to the concentration immediately before saline or IGF-I administration.

Administration of IGF-I at a dose of 20 ug/kg and 30 ug/kg resulted in a decrease ($p<0.05$) at 30 minutes from 3.5 to 2.8 and 2.5 mmol/L, respectively.

The plasma catecholamine concentrations were below the minimal detectable level of the assay employed (50 ng/ml) both before and following IGF-I (all doses) or saline administration.
Cardiac Output:

The cardiac output, mean arterial pressure and pulse rate did not change significantly following the administration of saline or a 15 ug/kg bolus of IGF-I.

Following a bolus of 20 ug/kg of IGF-I the cardiac output increased ($p<0.05$) from 2.7±0.8 L/min to a maximum value of 3.6 ±0.9 L/min 40 minutes following IGF-I administration. Similarly, following a bolus of 30 ug/kg of IGF-I, the cardiac output increased ($p<0.05$) from 2.1±0.5 L/min (mean arterial pressure 95±2 mmHg, pulse rate 130±20 beats/min) to a maximum value of 2.8±0.3 L/min (mean arterial pressure 104±8 mmHg, pulse rate 140±20 beats/min) 30 minutes following IGF-I administration. Thereafter cardiac output returned to that observed immediately before IGF-I administration.

In FIG. 1 the percentage change in cardiac output (CO) following a bolus of rhIGF-I given at time =60 minutes is shown. The change is calculated as percentage of mean basal pre-infusion values (time −60 to 0 ).

It is clearly seen that the cardiac output is increased after a higher dose of IGF-I has been administered. This increase does not give a change in pulse rate.

Figure 2:
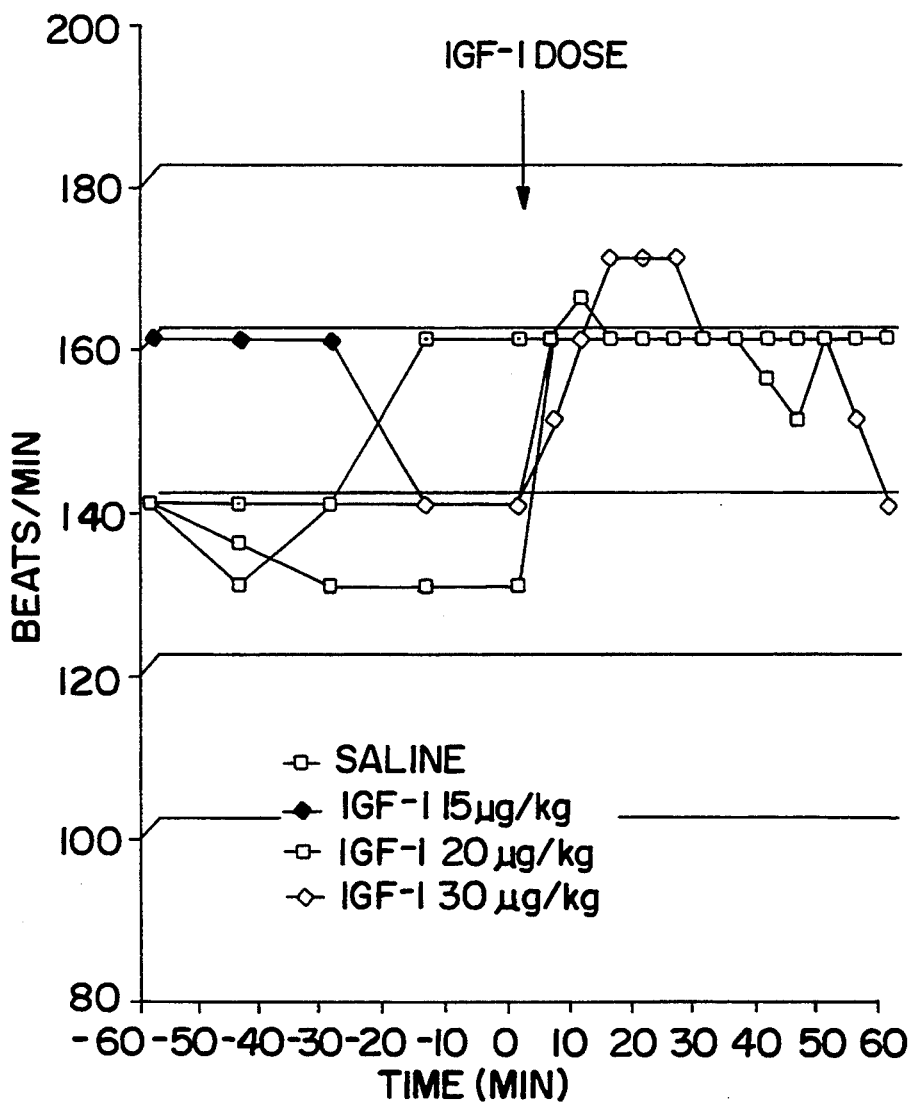
FIG. 2 shows the pulse rates after IGF-I dosing

FIG. 2 shows the pulse rates after IGF-I dosing. It is clearly seen that the pulse rate has not been significantly changed.

Figure 3:
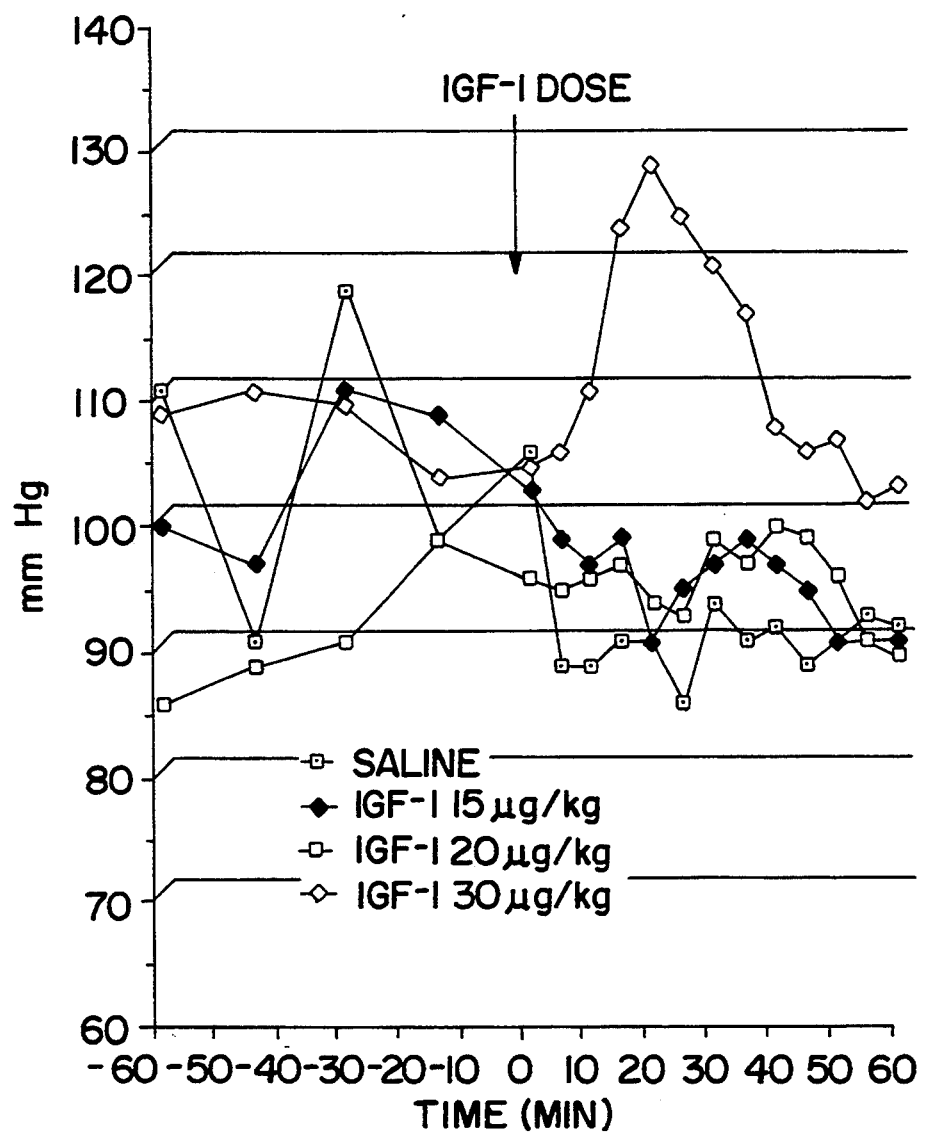
FIG. 3 shows the mean arterial pressure after IGF-I dosing.

FIG. 3 shows the mean arterial pressure after IGF-I dosing, based on the following figures, see Table 3.

TABLE 3

| | Mean arterial pressure, L | | | |
|---|---|---|---|---|
| | IGF-I (μg/kg) | | | |
| Min | 0 | 15 | 20 | 30 |
| −60 | 110 ± 12 | 99 ± 10 | 85 ± 15 | 108 ± 8 |
| −45 | 90 ± 15 | 96 ± 10 | 88 ± 12 | 110 ± 10 |
| −30 | 118 ± 13 | 110 ± 12 | 90 ± 17 | 109 ± 16 |
| −15 | 98 ± 14 | 108 ± 8 | 98 ± 12 | 103 ± 11 |
| 0 | 105 ± 17 | 102 ± 12 | 95 ± 20 | 104 ± 18 |
| 5 | 88 ± 18 | 98 ± 14 | 94 ± 13 | 104 ± 12 |
| 10 | 88 ± 17 | 96 ± 12 | 95 ± 12 | 110 ± 17 |
| 15 | 90 ± 12 | 98 ± 14 | 96 ± 10 | 123 ± 18 |
| 20 | 90 ± 15 | 90 ± 12 | 93 ± 15 | 128 ± 19 |
| 25 | 85 ± 14 | 94 ± 16 | 92 ± 16 | 120 ± 9 |
| 30 | 93 ± 12 | 96 ± 10 | 98 ± 14 | 120 ± 11 |
| 35 | 90 ± 11 | 98 ± 12 | 96 ± 9 | 116 ± 19 |
| 40 | 91 ± 10 | 96 ± 10 | 99 ± 17 | 107 ± 5 |
| 45 | 88 ± 12 | 94 ± 15 | 98 ± 13 | 105 ± 14 |
| 50 | 90 ± 15 | 90 ± 8 | 95 ± 7 | 106 ± 13 |
| 55 | 92 ± 10 | 90 ± 7 | 90 ± 10 | 101 ± 9 |
| 60 | 91 ± 16 | 90 ± 12 | 89 ± 19 | 102 ± 5 |

Example 5

The aim of the study was to see whether IGF-I therapy could improve cardiac performance in rats which had cardiac failure secondary to chronic adriamycin therapy. (Adriamycin induces cardiomyopathy)

60-day-old Wistar rats were divided into three groups:

1. Controls, saline subcutaneously, weekly, for 12 weeks.
2. Adriamycin 2 mg/kg subcutaneously, Weekly, for 12 weeks. This group had saline pumps inserted and were treated with saline for the last 4 weeks.
3. Adriamycin 2 mg/kg subcutaneously, weekly, for 12 weeks plus IGF-I 0.8 mg/kg/day subcutaneously by osmotic minipumps for the last 4 weeks.

At the end of the study the surviving rats were anaethetised and cardiac outputs obtained by the classical microsphere method. 10 out of 25 of the adriamycin treated animals, group 2, survived to anaesthesia and 9 out of 16 rats treated with IGF-I plus adriamycin, group 3.

All data from the study are I summarized in Table 4.

7 saline plus adriamycin treated and 5 adriamycin plus IGF-I treated rats completed the cardiac output studies in an acceptable condition (with a basal heart rate >300 beats/min). In addition, data was available on 7 control rats. The cardiac output (ml/min) was:

1. controls 136.1±14.1
2. adriamycin plus saline 91.4±17.1
3. adriamycin plus IGF-I 131.9±16.3.

The effect of IGF-I to improve cardiac output in adriamycin treated rats was highly significant ($p<0.01$) and the adriamycin reduced cardiac output was largely restored by IGF-I.

When expressed as cardiac index to adjust for body weight (ml/min/kg) the effect of IGF-I was still significant although the effect of adriamycin relative to saline litter-mates was less apparent due to the catabolic state of the adriamycin treated animals. However, this measure is confounded as bodyweight is affected by variable water retention.

Cardiac index (ml/min/kg):
1. controls 241.8±19.3
2. adriamycin 229.7±25.4
3. adriamycin +IGF-I 310±38.8

The heart rate (beats/rain) did not differ between the groups:
1. controls 410±44
2. adriamycin 410±62
3. adriamycin +IGF-I 395±80

However, the stroke volume (ml) did improve with IGF-I therapy
1. controls 0.335±0.05
2. adriamycin 0.226±0.05
3. adriamycin +IGF-I 0.323±0.07

Animals were weighed weekly during the treatment period.

In animals surviving 12 weeks also organ weights were measured as well as ascitic fluid and pleural effusion volumes.

TABLE 4

Preliminary results summary - IGF-I treatment in Adriamycin induced cardiomyopathy

| Means ± SD | Controls | Adriamycin | Adriamycin plus IGF-I |
|---|---|---|---|
| Weight change (g) | 229.5 ± 43.8 | 88.5 ± 48.6 | 87.9 ± 51.5 |
| | n = 24 | n = 11 | n = 9 |
| Liver weight (g) | 20.9 ± 3.8 | 17.7 ± 1.9 | 17.0 ± 2.2 |
| | n = 9 | n = 11 | n = 9 |
| Spleen weight (g) | 1.15 ± 0.23 | 0.78 ± 0.10 | 0.93 ± 0.33 |
| | n = 9 | n = 11 | n = 9 |
| Lung weight (g) | 1.94 ± 0.30 | 1.56 ± 0.23 | 1.90 ± 0.29 |
| | n = 9 | n = 11 | n = 9 |
| L Kidney wt (g) | 1.87 ± 0.24 | 1.91 ± 0.28 | 2.36 ± 0.49[1] |
| | n = 9 | n = 11 | n = 9 |
| R Kidney wt (g) | 1.92 ± 0.20 | 1.83 ± 0.31 | 2.33 ± 0.45[1] |
| | n = 9 | n = 11 | n = 9 |
| Ascites (ml) | 0.9 ± 1.1 | 50.0 ± 38.1 | 21.4 ± 22.1[2] |
| | n = 7 | n = 11 | n = 9 |
| Pleural effusion (ml) | 0 | 5.5 ± 4.0 | 3.7 ± 3.7 |
| Cardiac output (ml/min) | 136.1 ± 14.1 | 91.4 ± 17.1 | 131.9 ± 16.3[1] |
| | n = 7 | n = 7 | n = 5[3] |
| Cardiac output (index) (ml/min/kg) | 241.7 ± 19.3 | 229.7 ± 25.4 | 310.4 ± 38.8 |
| | n = 7 | n = 7 | n = 5[4] |
| Stroke volume (ml) | 0.335 ± 0.052 | 0.226 ± 0.46 | 0.323 ± 0.070 |
| | | | n = 5[5] |
| Systolic pressure (mmHg) | 114.4 ± 15.0 | 75.7 ± 16.2 | 82.2 ± 32.4 |
| | | | n = 5[6] |

Notes:
Statistics employed ANOVA wkh planned comparisons between Adriamycin and Adriamycin + IGF-I groups.
1 p = 0.002
2 p = 0.06
3 p = 0.005
4 p = 0.002
5 p = 0.009
6 N.S.

The conclusion is apparent that 4 weeks of IGF-I therapy improves cardiac performance in cardiac myopathy.

The two aspects of the present invention, promoting net protein synthesis in the heart muscle and improving cardiac output by increasing stroke volume, have different IGF-I dose dependencies. Thus, in clinical cases where increased stroke volume should be desirable for the patient without increased heart rate, this will be possible by selection of a suitable dose. Furthermore, stimulation of heart muscle protein synthesis can be achieved separately by administration of lower doses of IGF-I.

Finally, it has to be understood that various other modifications and/or alterations may be made without departing from the spirit of the present invention as outlined herein.

We claim:

1. A method for increasing cardiac muscle protein synthesis and for treating cardiomyopathies, acute heart failure or acute insult comprising administering to a mammalian host in need thereof an effective amount of human IGF-I for increasing said cardiac muscle protein synthesis, and for treating said cardiomyopathies, acute heart failure or acute insult.

2. Method according to claim 1 for prevention of cardiomyopathies following drug administration, inflammation, infection, sepsis or ischaemia.

3. Method according to claim 1 for increasing the rate of recovery from cardiomyopathy, myocarditis, inflammation or myocardial ischaemia and infarction 4. Method according to claim 1 for improvement of cardiac output by increasing heart stroke volume.

5. Method according to claim 4 wherein said cardiac output is reduced as a result of trauma, sepsis, myocardial infarction, surgery, cardiac inflammation or a combination thereof.

6. Method according to claim 5 for treatment of myocardial infarction.

7. Method according to claim 1 in which human IGF-I is used.

8. Method according to claim 1 in which the dose administered is 0.01–10 mg/kg body weight/day.

9. Method according to claim 1, characterized in that the administration is subcutaneous, intramuscular, intravenous, intranasal, oral or dermal, or a combination of these administration methods.

10. Method according to claim 9, characterized in that the administration is subcutaneous.

11. The method of claim 8 wherein said dose is 0.1–2 mg/kg body weight/day.

12. The method of claim 11 wherein human IGF-I is administered.

13. The method of claim 8 wherein human IGF-I is administered.

* * * * *